United States Patent
Kaneko

(10) Patent No.: US 10,071,996 B2
(45) Date of Patent: Sep. 11, 2018

(54) OPTICAL ISOMER OF 1,4-BENZOTHIAZEPINE-1-OXIDE DERIVATIVE, AND PHARMACEUTICAL COMPOSITION PREPARED USING SAME

(71) Applicants: AETAS PHARMA CO., LTD., Tokyo (JP); Noboru Kaneko, Oyama-shi, Tochigi (JP)

(72) Inventor: Noboru Kaneko, Oyama (JP)

(73) Assignees: AETAS PHARMA CO., LTD., Tokyo (JP); Noboru Kaneko, Oyama-shi (JP)

( * ) Notice: Subject to any disclaimer, the term of this patent is extended or adjusted under 35 U.S.C. 154(b) by 0 days.

(21) Appl. No.: 15/329,827

(22) PCT Filed: Jul. 17, 2015

(86) PCT No.: PCT/JP2015/070488
§ 371 (c)(1),
(2) Date: Jan. 30, 2017

(87) PCT Pub. No.: WO2016/017448
PCT Pub. Date: Feb. 4, 2016

(65) Prior Publication Data
US 2017/0247362 A1    Aug. 31, 2017

(30) Foreign Application Priority Data
Jul. 30, 2014 (JP) ................... 2014-155068

(51) Int. Cl.
*C07D 417/06*    (2006.01)

(52) U.S. Cl.
CPC ........ *C07D 417/06* (2013.01); *C07B 2200/07* (2013.01)

(58) Field of Classification Search
CPC .................................................. C07D 417/06
See application file for complete search history.

(56) References Cited

U.S. PATENT DOCUMENTS

| | | | |
|---|---|---|---|
| 5,416,066 A | 5/1995 | Kaneko et al. | |
| 5,929,244 A | 7/1999 | Von Unge | |
| 6,506,745 B1 | 1/2003 | Aisaka et al. | |
| 6,977,252 B1 | 12/2005 | Kaneko et al. | |
| 2005/0032866 A1 | 2/2005 | Bonhomme et al. | |
| 2007/0219180 A1 | 9/2007 | Kaneko | |
| 2010/0029578 A1 | 2/2010 | Olgin et al. | |
| 2010/0160639 A1 | 6/2010 | Singh et al. | |
| 2011/0306594 A1 | 12/2011 | Kaneko et al. | |
| 2013/0137768 A1 | 5/2013 | Lantoine-Adam et al. | |
| 2014/0088171 A1 | 3/2014 | Yan et al. | |

FOREIGN PATENT DOCUMENTS

| | | |
|---|---|---|
| EP | 2 402 333 A1 | 1/2012 |
| JP | 11-508590 A | 7/1999 |
| JP | 2000-247889 A | 9/2000 |
| JP | 2001-31571 A | 2/2001 |
| JP | 2003-95977 A | 4/2003 |
| JP | 2003-267890 A | 9/2003 |
| JP | 2007-145869 A | 6/2007 |
| JP | 2009-513713 A | 4/2009 |
| JP | 2009-542624 A | 12/2009 |
| JP | 4808825 B2 | 11/2011 |
| JP | 2012-184225 A | 9/2012 |
| JP | 2013-538197 A | 10/2013 |
| WO | 92/12148 A1 | 7/1992 |
| WO | 97/02261 A1 | 1/1997 |
| WO | 2005/105793 A1 | 11/2005 |
| WO | 2010/098080 A1 | 9/2010 |

(Continued)

OTHER PUBLICATIONS

Kodama, "Guidelines for Drug Treatment of Arrhythmias", (2009); English translation only; original document cited in IDS dated Jan. 27, 2017. (2 pages).

Inoue, "Guidelines for Pharmacotherapy of Atrial Fibrillation", (2013); English translation only; original document cited in IDS dated Jan. 27, 2017. (2 pages).

International Search Report dated Sep. 1, 2015, issued in counterpart International Application No. PCT/JP2015/070488 (2 pages).

Written Opinion of the International Searcing Authority (Form PCT/ISA/237) dated Sep. 1, 2015, issued in counterpart International Application No. PCT/JP2015/070488 (5 pages).

Kodama, "Guidelines for Drug Treatment of Arrhythmias", (2009). (82 pages).

(Continued)

*Primary Examiner* — Bruck Kifle
(74) *Attorney, Agent, or Firm* — Westerman, Hattori, Daniels & Adrian, LLP

(57) ABSTRACT

The present invention provides: a novel compound which is characterized by being capable of increasing the number of heart beats or a blood pressure mildly to improve hemodynamics, and which is useful as a therapeutic or prophylactic agent for atrial fibrillation and heart failure; and a pharmaceutical composition which contains the compound. The present invention relates to: an optical isomer of a 1,4-benzothiazepine-1-oxide derivative represented by general formula [II]

[II]

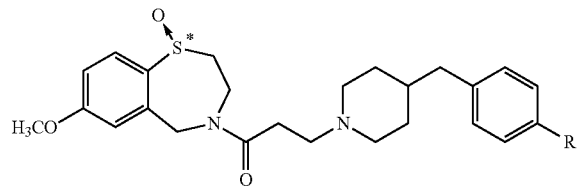

(wherein R represents a hydrogen atom or a hydroxy group; and * indicates the presence of an optical isomer) or a pharmaceutically acceptable salt thereof; and a pharmaceutical composition which contains the optical isomer or a pharmaceutically acceptable salt thereof.

7 Claims, 5 Drawing Sheets

(56) References Cited

FOREIGN PATENT DOCUMENTS

WO 2010/114562 A1 10/2010

OTHER PUBLICATIONS

Inoue., "Guidelines for Pharmacotherapy of Atrial Fibrillation", (2013). (60 pages).
Echt et., "Mortality and Morbidity in Patients Receiving Encainide, Flecainide, or Placebo", The New England Journal of Medicine, Mar. 21, 1991, vol. 324, No. 12. (8 pages).
Translation of Written Opinion of the International Searching Authority (Form PCT/ISA/237) dated Sep. 1, 2015, issued in counterpart International Application No. PCT/JP2015/070488 (6 pages).
Extended (supplementary) European Search Report dated Dec. 1, 2017, issued in counterpart European Application No. 15826775.7. (7 pages).

[Fig. 1]
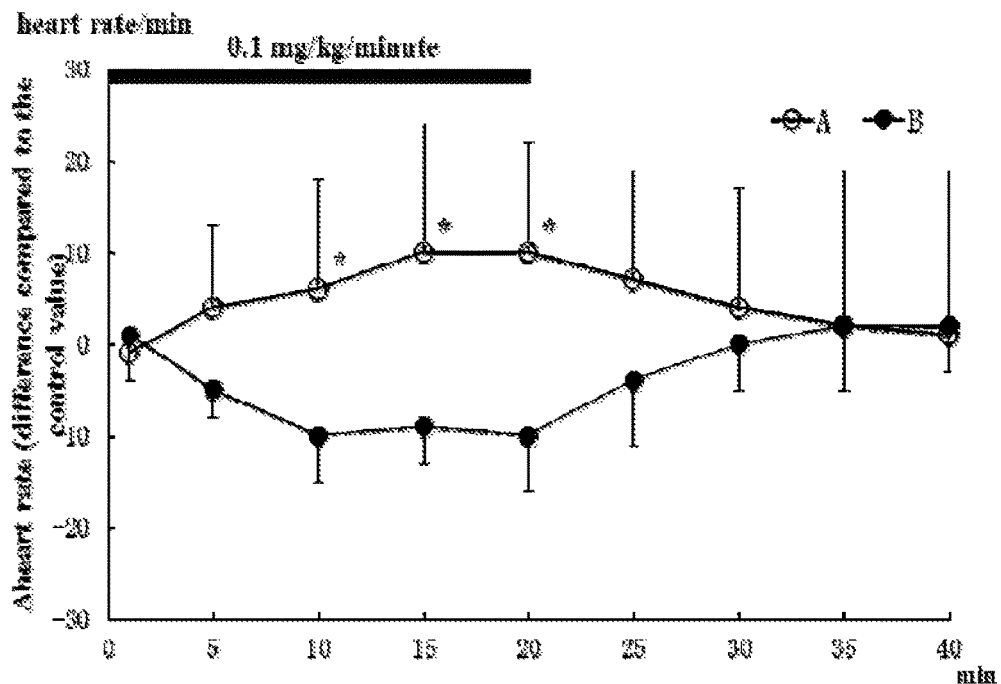
[Fig. 2]
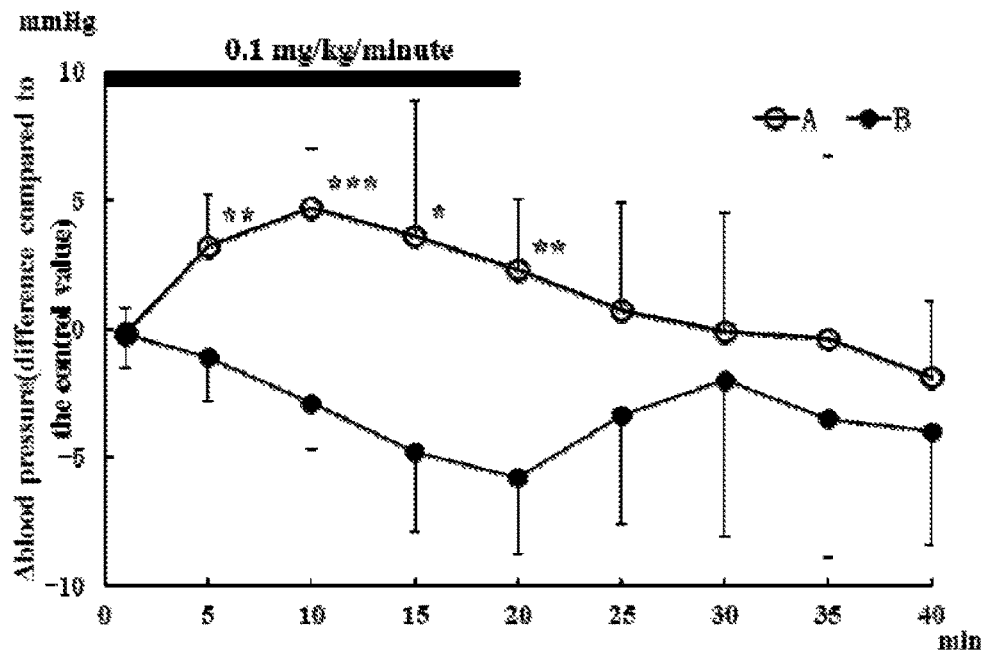

[Fig. 3]
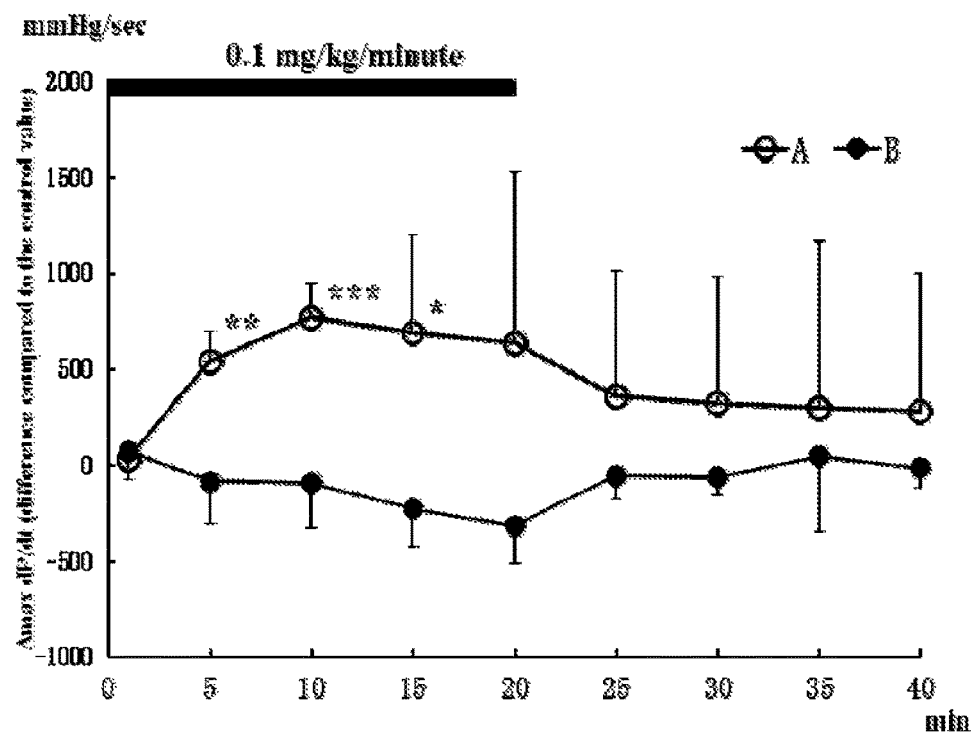
[Fig. 4]
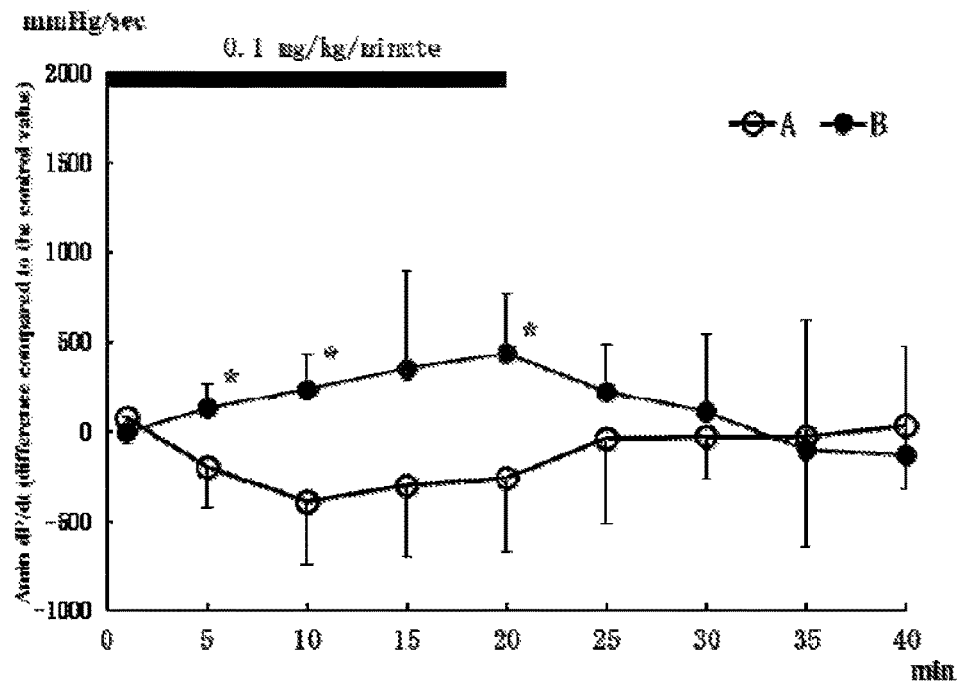

[Fig. 5]
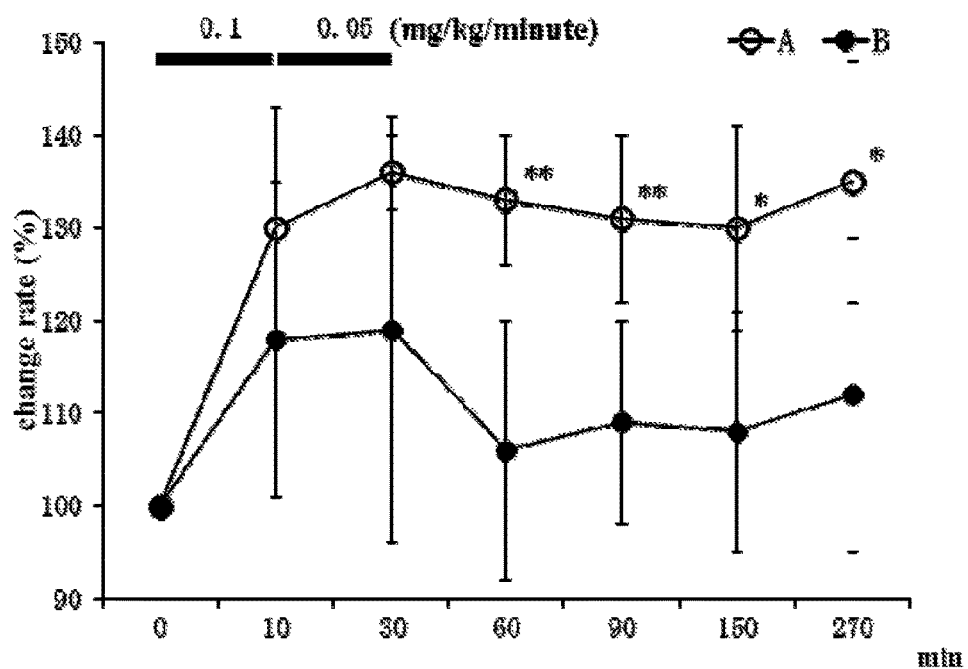
[Fig. 6]
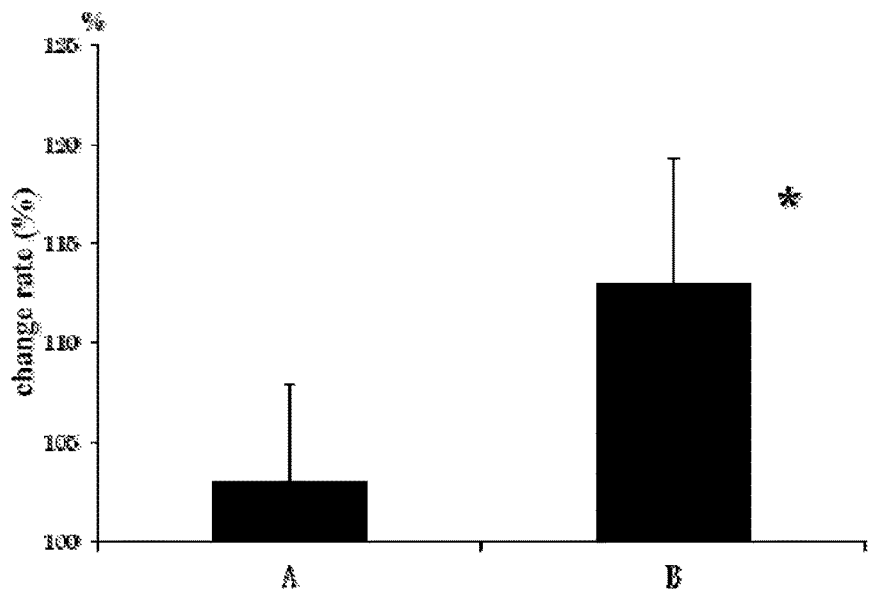

[Fig. 7]
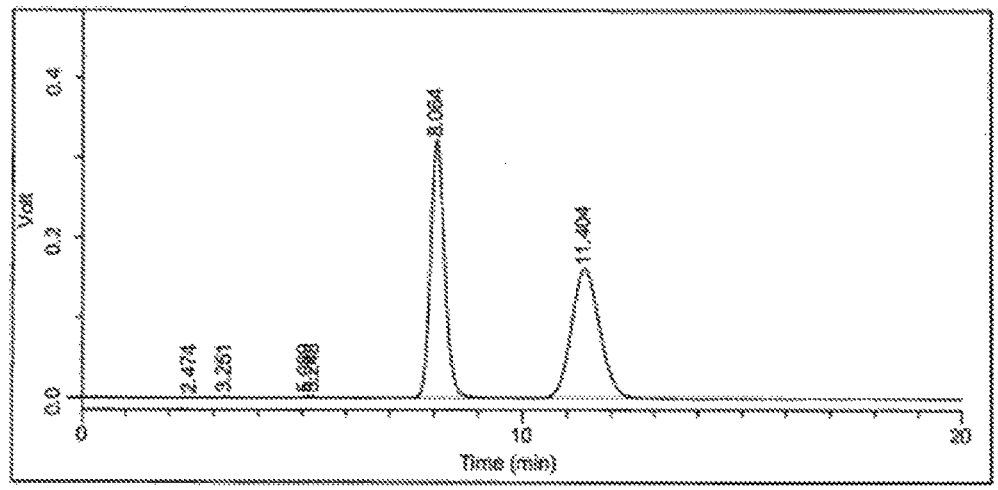
[Fig. 8]
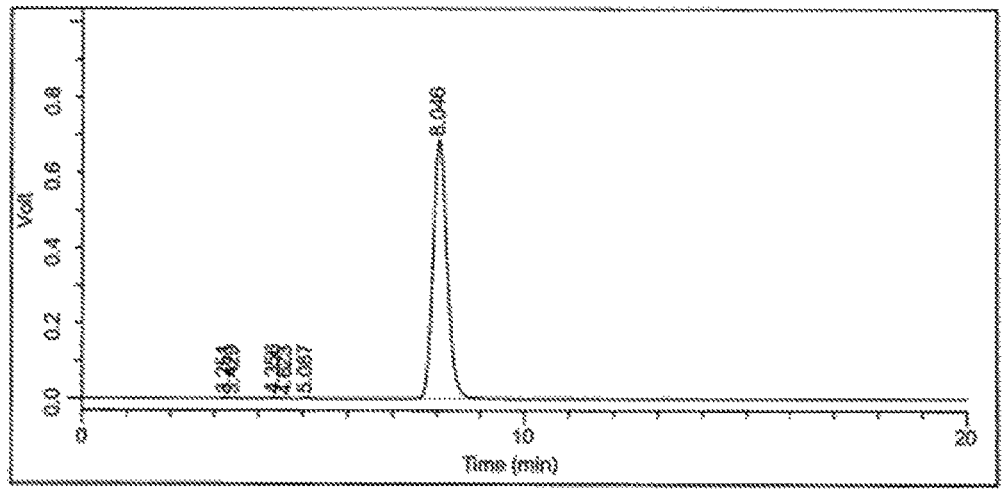

[Fig. 9]
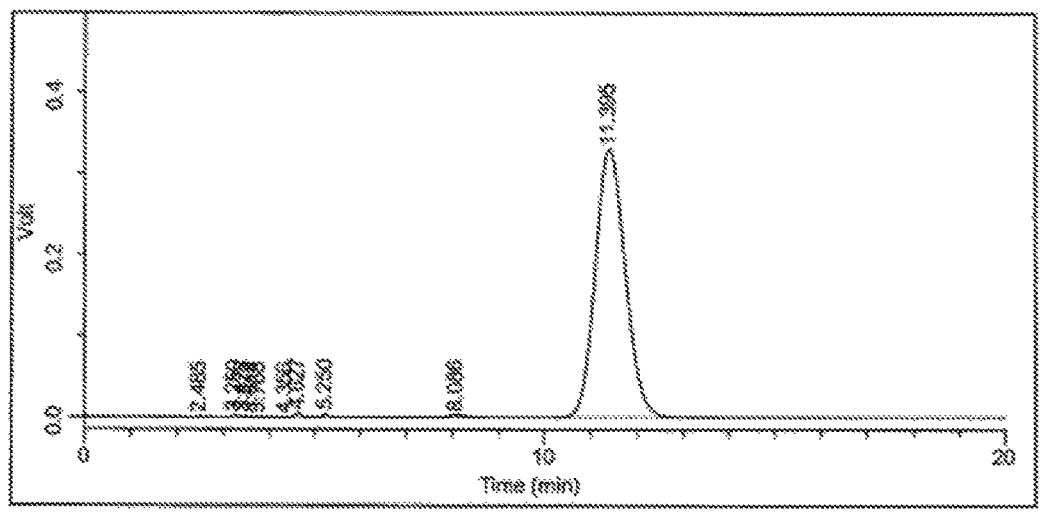

OPTICAL ISOMER OF 1,4-BENZOTHIAZEPINE-1-OXIDE DERIVATIVE, AND PHARMACEUTICAL COMPOSITION PREPARED USING SAME

TECHNICAL FIELD

The present invention relates to an optical isomer of a 1,4-benzothiazepine-1-oxide derivative represented by the general formula [I] of the present invention or a pharmaceutically acceptable salt thereof, and a pharmaceutical composition using the optical isomer or a pharmaceutically acceptable salt thereof.

BACKGROUND ART

Arrhythmia is classified into brady arrhythmia and tachy arrhythmia. Tachy arrhythmia is further classified into atrial arrhythmia and ventricular arrhythmia depending on a site of onset. Atrial tachy arrhythmia includes atrial fibrillation, atrial flutter, supraventricular tachycardia, and atrial extrasystole. Ventricular tachy arrhythmia includes ventricular fibrillation, ventricular flutter, ventricular tachycardia, and ventricular extrasystole.

Anti-arrhythmic agents have been used for treatment and prophylaxis of those tachy arrhythmias.

Currently, for classification of anti-arrhythmic agents, Vaughan Williams classification or Sicilian Gambit classification in which anti-arrhythmic agents are classified based on their receptors or target molecules is used.

Class I agents in the Vaughan-Williams classification correspond to Na channel blockers, which decrease the maximum rate of rise of action potential. Class I agents are further divided into three subgroups, i.e., Class Ia agents which can extend action potential duration and include quinidine, procainamide, and disopyramide, Class Ib agents which can shorten action potential duration and include lidocaine, and Class Ic agents which are Na channel blockers to extend refractory period by decreasing the maximum rate of rise of action potential and that include flecainide, propafenone, and pilsicainide. Class II agents area blockers. Class III agents are $K^+$ channel blockers, and by inhibiting potential-dependent $K^+$ channel, that lengthen the action potential duration and extend the effective refractory period. Examples of the $K^+$ channel blocker include amiodarone, sotalol, and nifekalant. Class IV agents are Ca antagonists.

Among tachy arrhythmias, atrial fibrillation is representative arrhythmia which causes irregular systole of an atrium at 250 to 400 times per minute, or at even higher frequency. Atrial fibrillation is the greatest risk factor for causing heart failure and cardiogenic cerebral infarction, and converting atrial fibrillation to normal heart rhythms and preventing an occurrence of atrial fibrillation remain as an urgent and vital issue (see, Non Patent Document 1 and 2).

Atrial fibrillation is well known to occur based on high blood pressure, myocardial infarction, heart failure or the like as an underlying disorder. However, even without any organic heart disease, it may occur according to aging. The onset frequency starts to increase dramatically in people in their 60s, and it is known that the onset frequency is almost 10% in people over 80. In Japan, about 700,000 people fall ill every year, and number of patients who fall ill in Europe and USA is presumably 7,500,000.

As a therapeutic agent for atrial fibrillation, a pharmaceutical preparation selected from Class Ia, Class Ic, and Class III is used. However, the problem of those pharmaceutical preparations is that the atrial fibrillation stopping rate for getting back sinus rhythm from atrial fibrillation is as low as 30 to 40%. Furthermore, the pharmaceutical preparations selected from Class Ia and Class Ic decrease heart rate and blood pressure to deteriorate cardiac function. Furthermore, the pharmaceutical preparations selected from Class Ia, Class Ic, and Class III extend effective refractory period of ventricle and cause fatal arrhythmia such as Torsades de Pointes (ventricular tachycardia) or ventricular fibrillation. It was found according to a large-scale clinical trial CAST that, compared to a placebo, pharmaceutical preparations of Class Ic rather increase mortality in a patient with arrhythmia after myocardial infarction (see, Non Patent Document 3) and use of such pharmaceutical preparations is prohibited for arrhythmia of a patient with ischemic cardiac disease.

As described above, the action of lowering heart rate or blood pressure, inhibiting myocardial contraction or relaxation, or fatal proarrhythmic potential of anti-arrhythmic agents remains as a huge problem of drug therapy for atrial fibrillation.

An episode of atrial fibrillation restricts blood inflow from an atrium to a ventricle, and then yields a deterioration of cardiac function. As such, a heart failure is often caused. Furthermore, an episode of atrial fibrillation is often based on a heart failure as an underlying disorder and the therapeutic agent itself may cause a heart failure. Thus, application of drug therapy is very difficult for a patient with atrial fibrillation who shows lowered cardiac function. In particular, in case of a treatment of arrhythmia caused by atrial fibrillation, a pharmaceutical agent which shows a potent action on an atrium while not showing any effect on a ventricle is not developed yet. Thus, even if it is desired to solely extend the atrial effective refractory period, a ventricle is also affected so that the ventricular effective refractory period is also extended. For such reasons, a more potent therapeutic agent for arrhythmia caused by atrial fibrillation has a higher proarrhythmic potential like ventricular fibrillation as a side effect. Thus, a pharmaceutical agent which is useful for fixing atrial fibrillation to NSR (normal sinus rhythm) with a high selectivity and certainty while exhibiting no effect on cardiac function and having no proarrhythmic potential is not discovered at the present moment.

As prophylactic or therapeutic agents for atrial fibrillation or arrhythmia in atrial cells, diazepine compounds having an atrial selective $K^+$ channel blocking action (see, Patent Document 1), 5-$HT_4$ receptor antagonists (see, Patent Documents 2 and 3), p38 inhibitors (see, Patent Document 4), and pantenyl docosahexaenoate (see, Patent Document 5) are reported. Furthermore, the inventor of the present invention reported 4-[3-(4-benzylpiperidin-1-yl)propionyl]-7-methoxy-2,3,4,5-tetrahydro-1,4-benzothiazepine which has an inhibitory action on KD (kinetic cell death) of myocardium and is effective for myocardial necrosis or acute myocardial infarction without being accompanied by cardiodepressant effect (see, Patent Documents 6 and 7).

However, although all of those substances have been described to have an excellent anti-atrial fibrillation action like the effect of recovering normal sinus rhythm or lengthening atrial effective refractory period, there is no description about the suppression effect for proarrhythmic potential, which is a side effect of anti-arrhythmic agents.

There are many reports regarding 4-[3-(4-benzylpiperidin-1-yl)propionyl]-7-methoxy-2,3,4,5-tetrahydro-1,4-benzothiazepine and a derivative thereof (see, Patent Documents 6 and 7). For example, it has been reported that the compound has an action of promoting the effect of carcinostatic agents (see, Patent Document 8) or an action of inhibiting the leak of $Ca^{2+}$ from the sarcoplasmic reticulum by amelioration and/or stabilization of ryanodine receptor function (see, Patent Document 9), or the compound is useful as a muscle relaxation accelerator, a therapeutic agent for left ventricular diastolic dysfunction, a therapeutic agent for angina pectoris, a therapeutic agent for acute pulmonary edema, a blood ameliorant for microcirculation system, a therapeutic agent for hypertension, a therapeutic agent for ventricular tachycardia, and a therapeutic agent for Torsade de pointes (see, Patent Document 10).

It is recently found that 4-[3-(4-benzylpiperidin-1-yl)propionyl]-7-methoxy-2,3,4,5-tetrahydro-1,4-benzothiazepine-1-oxide (see, Patent Document 11), which has been developed by the inventor of the present invention, also is useful as a therapeutic or prophylactic agent for myocardium relaxation disorder that is observed in atrial arrhythmia as well as heart failure or high blood pressure, diastolic dysfunction, angina pectoris or myocardial infarction, hypertensive disease, or ischemic heart disease, heart failure, and ventricular arrhythmia. However, the selective action on atrial arrhythmia, in particular atrial fibrillation, is not confirmed. Instead, as a strong action on ventricle has been confirmed, it is expected that the proarrhythmic potential cannot be avoided when the compound is used for treatment of atrial fibrillation, for example.

As described above, the conventional pharmaceutical preparations suggested as therapeutic agents for atrial fibrillation or atrial arrhythmia, including 1,4-benzothiazepine-1-oxide derivative, have been found to have high effectiveness in terms of an anti-atrial fibrillation action. However, there are many cases in which the higher action on a ventricle is shown compared to the effectiveness for atrial fibrillation, and thus a problem occurs in that the proarrhythmic potential is negligible.

Under the circumstances, it is strongly desired to have a pharmaceutical preparation which enables recovery of atrial fibrillation to normal sinus rhythm and has no proarrhythmic potential.

CITATION LIST

Patent Document

Patent Document 1: JP 2012-184225 A
Patent Document 2: JP 2003-267890 A
Patent Document 3: JP 2007-145869 A
Patent Document 4: JP 2009-513713 A
Patent Document 5: JP 2013-538197 A
Patent Document 6: WO 92/12148 A
Patent Document 7: JP 2000-247889 A
Patent Document 8: JP 2001-31571 A
Patent Document 9: JP 2003-95977 A
Patent Document 10: WO 2005/105793 A1
Patent Document 11: JP 4808825 B2

Non Patent Document

Non Patent Document 1: Joint working group of The Japanese Circulatory Society, Japanese Society of Pediatric Cardiology and Cardiac Surgery, Japanese College of Cardiology, Japanese Society of Electrocardiology, and Japanese Arrhythmia Society "Guidelines for Drug Treatment of Arrhythmias" (revised version, 2009)
Non Patent Document 2: Joint working group of The Japanese College of Cardiology, Japanese Society of Electrocardiology, and Japanese Arrhythmia Society "Guidelines for (Drug) Treatment of Atrial Fibrillation" (revised version, 2013)

Non Patent Document 3: Echt D S et al., N Engl. J. Med. 324 (12): 781-788 (1991)

SUMMARY OF THE INVENTION

Problems to be Solved by the Invention

The present invention provides a novel compound having a useful pharmaceutical action like promoting myocardial contraction and relaxation, and a pharmaceutical composition using the compound which is useful as a therapeutic agent and/or prophylactic agent for a heart disorder such as arrhythmia or heart failure.

The present invention further provides a pharmaceutical composition which is useful as a therapeutic agent for atrial fibrillation as it can mildly increase the heart rate or blood pressure to improve cardiac functions and, in particular, is useful as a therapeutic agent for atrial arrhythmia that does not cause ventricular arrhythmia as it solely extends atrial effective refractory period but not extends ventricular effective refractory period.

Means to Solve the Problems

The inventor of the present invention has examined various pharmaceutical actions of 4-[3-(4-benzylpiperidin-1-yl)propionyl]-7-methoxy-2,3,4,5-tetrahydro-1,4-benzothiazepine-1-oxide represented by the following general formula [I] and a derivative thereof.

[Chem. 1]

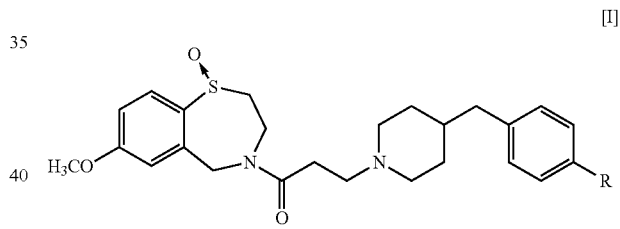

(in the formula, R represents a hydrogen atom or a hydroxyl group).

Furthermore, the inventor reported in Patent Document 11 that the 1,4-benzothiazepine-1-oxide derivative compound of the general formula [I] has an action of enhancing myocardial diastolic function, an action of mildly dilating coronary arteries, and a property of mildly lowering mildly the heart rate, and the compound also has a property of reducing oxygen consumption by cardiomyocytes together with increasing the oxygen supply to cardiomyocytes, and thus the compound can be safely used even for a patient of advanced age, a patient with high blood pressure or left ventricular diastolic dysfunction like left ventricular hypertrophy, a patient with heart failure or heart failure caused by diastolic dysfunction, or a patient with angina pectoris or myocardial infarction, and also the compound is useful as a therapeutic agent or prophylactic agent for myocardial relaxation disorder, hypertension, or the like. Meanwhile, according to the compound represented by the general formula [I], the sulfur atom in the S-oxide part is a chiral center so that the compound has central chirality. The inventor of the present invention tried to separate stereoisomers related to the central chirality, and as a result, stable separation is achieved even at 40° C. Accordingly, the inventor succeeded in isolating each enantiomer. In the present specification, between two enantiomers that are separated by the inventor by using a chiral column, the first eluted enantiomer is referred to as a first component (it may be alternatively referred to as the compound (A)), and the next eluted enantiomer is referred to as a second component (it may be alternatively referred to as the compound (B)) (see, FIG. 7). Ratio between the separated first component and second component was approximately 1:1 (see, FIG. 7).

Furthermore, the inventor of the present invention collected each of the two enantiomers (hereinbelow, also referred to as optical isomers) (see, FIGS. 8 and 9).

Furthermore, as a result of determining the pharmacological activity of both of them, it was surprisingly found that the first optical isomer component (A) and second optical isomer component (B) have a contradictory action so that, regarding atrial fibrillation in particular, only the first component (A) has a very specific pharmaceutical activity from which a high anti-atrial fibrillation effect and an effect of lowering proarrhythmic potential are expected.

Namely, the first optical isomer component mildly increases heart rate and blood pressure to enhance the heart contraction and relaxation function. On the other hand, the second optical isomer component decreases heart rate and blood pressure to lower the heart contraction and relaxation function. Furthermore, the atrial effective refractory period is extended more by the first optical isomer component than by the second component, and the first optical isomer component does not extend the ventricular effective refractory period but the second optical isomer component can extend the ventricular effective refractory period in a concentration dependent manner. This result indicates that the first optical isomer component hardly causes Torsades de Pointes or ventricular fibrillation but the second optical isomer component has a risk of causing those arrhythmias.

As described above, it was found that one enantiomer (the first component) between the compounds represented by the general formula [I] has, compared to the other enantiomer (the second component), a specific and ideal anti-atrial fibrillation effect of extending the atrial effective refractory period while not extending the ventricular effective refractory period so that, as a therapeutic agent for arrhythmia, in particular atrial fibrillation, it is an ideal pharmaceutical preparation having no proarrhythmic potential.

Furthermore, as the other enantiomer (the second component) also has a certain pharmaceutical action, it is useful as a pharmaceutical agent.

That is, the present invention relates to optical isomers of a 1,4-benzothiazepine-1-oxide derivative represented by the following general formula [II] or a pharmaceutically acceptable salt thereof;

[Chem. 2]

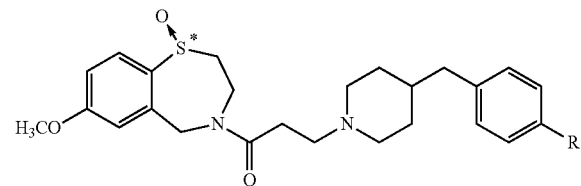

[II]

(in the formula, R presents a hydrogen atom or a hydroxyl group, and * indicates the presence of optical isomers). In greater detail, it relates to the first optical isomer component of a 1,4-benzothiazepine-1-oxide derivative which is represented by the general formula [II] above or a pharmaceutical acceptable salt thereof.

The present invention also relates to a pharmaceutical composition containing the first optical isomer component of a 1,4-benzothiazepine-1-oxide derivative which is represented by the general formula [II] above or a pharmaceutical acceptable salt thereof, and a pharmaceutically acceptable carrier.

Detailed explanations of the present invention are as described below.

(1) An optical isomer of 1,4-benzothiazepine-1-oxide derivatives represented by the following general formula [II] or a pharmaceutically acceptable salt thereof.

(2) The optical isomer of the 1,4-benzothiazepine-1-oxide derivatives or the pharmaceutically acceptable salt thereof described in the above (1), wherein the optical isomer of the 1,4-benzothiazepine-1-oxide derivatives represented by the general formula [II] above is a first optical isomer component.

(3) The optical isomer of the 1,4-benzothiazepine-1-oxide derivatives or the pharmaceutically acceptable salt thereof described in the above (1) or (2), wherein the pharmaceutically acceptable salt of the optical isomer of the 1,4-benzothiazepine-1-oxide derivatives is hydrochloride salt.

(4) A pharmaceutical composition comprising the optical isomer of the 1,4-benzothiazepine-1-oxide derivatives or the pharmaceutically acceptable salt thereof described in any one of the above (1) to (3), and a pharmaceutically acceptable carrier.

(5) The pharmaceutical composition described in the above (4), wherein the optical isomer of the 1,4-benzothiazepine-1-oxide derivatives represented by the general formula [II] above is a first optical isomer component.

(6) The pharmaceutical composition described in the above (4) or (5), which is a therapeutic agent and/or a prophylactic agent for a heart disorder.

(7) The pharmaceutical composition described in the above (6), wherein the heart disorder is arrhythmia, heart failure, angina pectoris, or myocardial infarction.

(8) The pharmaceutical composition described in the above (7), wherein the arrhythmia is atrial fibrillation and/or atrial flutter.

(9) The pharmaceutical composition described in the above (4) or (5), which is a therapeutic agent and/or a prophylactic agent for improving atrial fibrillation accompanied with reduced heart function.

(10) A method for producing an optical isomer represented by the general formula [II] above or a pharmaceutically acceptable salt thereof by resolving the compounds represented by the general formula [I] above and collecting each enantiomer.

(11) The method described in the above (10), wherein the enantiomer to be collected is a first optical isomer component.

(12) The method described in the above (10) or (11), wherein resolution is conducted by a method using a chiral column.

(13) The method described in the above (12), wherein the resolution is conducted by a method of collecting a component which is eluted first, as a first optical isomer component, by using a chiral column (CHIRALPAK AD-H size 0.46 cmI.D.×25 cmL.) and a mobile phase of MeOH/MeCN/DEA=90/10/0.1 (v/v) at flow rate of 1.0 mL/min.

(14) The method described in any one of the above (10) to (13), wherein the compounds represented by the general formula [I] above are produced by oxidizing a 1,4-benzothiazepine derivative represented by the following general formula [III]

[Chem. 3]

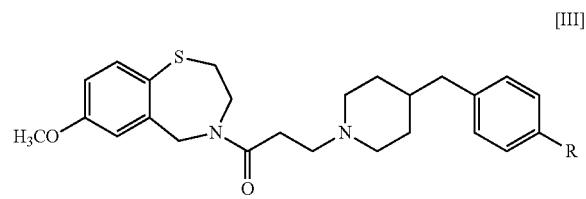

[III]

(in the formula, R presents a hydrogen atom or a hydroxyl group).

(15) The method described in the above (14), wherein the oxidation is oxidation by organic peroxide.

(16) A method for treating a heart disorder comprising administering to a patient with heart disorder a pharmaceutical composition comprising an effective amount of an optical isomer of 1,4-benzothiazepine-1-oxide derivatives represented by the general formula [II] above or a pharmaceutically acceptable salt thereof.

(17) The method described in the above (16), wherein the optical isomer of the 1,4-benzothiazepine-1-oxide derivatives represented by the general formula [II] is a first optical isomer component.

(18) The method described in the above (16) or (17), wherein the heart disorder is arrhythmia, heart failure, angina pectoris, or myocardial infarction.

(19) The method described in the above (18), wherein the arrhythmia is atrial fibrillation and/or atrial flutter.

(20) The method described in the above (16) or (17), wherein the heart disorder is atrial fibrillation accompanied with reduced heart function.

(21) An optical isomer of 1,4-benzothiazepine-1-oxide derivatives represented by the general formula [II] above or a pharmaceutically acceptable salt thereof to be used for a pharmaceutical composition for treatment and/or prophylaxis of a heart disorder.

(22) The optical isomer of the 1,4-benzothiazepine-1-oxide derivatives or the pharmaceutically acceptable salt thereof described in the above (21), wherein the optical isomer of the 1,4-benzothiazepine-1-oxide derivatives represented by the general formula [II] above is a first optical isomer component.

(23) The optical isomer or the pharmaceutically acceptable salt thereof described in the above (21) or (22), wherein the heart disorder is arrhythmia, heart failure, angina pectoris, or myocardial infarction.

(24) The optical isomer or the pharmaceutically acceptable salt thereof described in the above (23), wherein the arrhythmia is atrial fibrillation and/or atrial flutter.

(25) The optical isomer or the pharmaceutically acceptable salt thereof described in the above (21) or (22), wherein the heart disorder is atrial fibrillation accompanied with reduced heart function.

Effects of the Invention

The first optical isomer component represented by the general formula [II] of the present invention or a salt thereof has an action of mildly increasing the heart rate or blood pressure to improve a myocardial contraction and relaxation function. Such property is different from the property of the second optical isomer component, which is an enantiomer of the first optical isomer component represented by the general formula [II], and also from the property of the compound represented by the general formula [I] as a mixture of those components.

Accordingly, it is very surprising that the first optical isomer component represented by the general formula [II] of the present invention has a property which is completely different from that of the other enantiomer or a mixture thereof, and according to the present invention, it was found for the first time that the first optical isomer component can be collected and isolated.

Furthermore, the enantiomer of the second optical isomer component between the optical isomers represented by the general formula [II] of the present invention also has a certain pharmaceutical action, and thus it is useful as a component of a pharmaceutical preparation.

Furthermore, the first optical isomer component represented by the general formula [II] of the present invention or a salt thereof has an action of enhancing heart function and an action of mildly increasing the heart rate and blood pressure so that it can improve the heart function and is very useful as a pharmaceutical preparation for arrhythmia, in particular. Furthermore, the first optical isomer component represented by the general formula [II] of the present invention or a salt thereof can extend atrial effective refractory period without extending ventricular effective refractory period, and when administered to a beagle dog in an amount of up to 8 mg/Kg, it does not show any extension of ventricular effective refractory period. This is a very important result indicating that it is a very effective pharmaceutical preparation for atrial fibrillation and, at the same time, it does not have the side effect of a proarrhythmic potential. According to the present invention, a substance having very specific property of extending atrial effective refractory period without extending ventricular effective refractory period is identified for the first time in the world.

Meanwhile, at 1 mg/kg in a beagle dog, the second optical isomer component of the compound represented by the general formula [I] of the present invention can extend ventricular effective refractory period and also extend the ventricular effective refractory period in a dose dependent manner. Because extended ventricular effective refractory period may cause ventricular fibrillation or serious arrhythmia like Torsades de Pointes, even if it is a pharmaceutical preparation effective for atrial fibrillation, for example, it still has a side effect of proarrhythmic potential.

As described above, the present invention is to provide an ideal therapeutic agent and/or a prophylactic agent for arrhythmia which enables recovery of atrial fibrillation to normal sinus rhythm and has no proarrhythmic potential, and to provide a compound which is very useful not only for a pharmaceutical preparation to improve arrhythmia but also for a pharmaceutical preparation to improve heart failure.

Thus, the present invention is to provide a novel compound having those useful actions, and a pharmaceutical composition comprising the compound of the present invention.

BRIEF DESCRIPTION OF DRAWINGS

FIG. 1 illustrates that a change in the heart rate is compared as a difference compared to the previous value (i.e., control value) after administering (0.1 mg/kg/minute) the first optical isomer component of the present invention (in FIG. 1, expressed with an empty circle A) and the second component as the other enantiomer thereof (in FIG. 1, expressed with a solid circle B), respectively. As for the statistics, a significant difference between the first optical isomer component (in FIG. 1, expressed with an empty circle A) and the second component (in FIG. 1, expressed with a solid circle B) was examined by a t test. * indicates the significant difference P<0.05 between the first component and the second component.

FIG. 2 illustrates that a change in blood pressure is compared as a difference compared to the previous value (i.e., control value) after administering (0.1 mg/kg/minute) the first optical isomer component of the present invention (in FIG. 2, expressed with an empty circle A) and the second component as the other enantiomer thereof (in FIG. 2, expressed with a solid circle B), respectively. As the result of statistic analysis between the first optical isomer component (in FIG. 2, expressed with an empty circle A) and the second component (in FIG. 2, expressed with a solid circle B), the significant difference P<0.05 indicated by *, the significant difference P<0.01 indicated by , and the significant difference P<0.001 indicated by * were exhibited.

FIG. 3 illustrates that a change in myocardial contraction function (max dP/dt) is compared as a difference compared to the previous value (i.e., control value) after administering (0.1 mg/kg/minute) the first optical isomer component of the present invention (in FIG. 3, expressed with an empty circle A) and the second component as the other enantiomer thereof (in FIG. 3, expressed with a solid circle B), respectively. As the result of the statistic analysis between the first optical isomer component (in FIG. 3, expressed with an empty circle A) and the second component (in FIG. 3, expressed with a solid circle B), the significant difference P<0.05 indicated by *, the significant difference P<0.01 indicated by , and the significant difference P<0.001 indicated by * were exhibited.

FIG. 4 illustrates that a change in myocardial relaxation function (min dP/dt) is compared as a difference compared to the previous value (i.e., control value) after administering (0.1 mg/kg/minute) the first optical isomer component of the present invention (in FIG. 4, expressed with an empty circle A) and the second component as the other enantiomer thereof (in FIG. 4, expressed with a solid circle B), respectively. As the result of the statistic analysis between the first optical isomer component (in FIG. 4, expressed with an empty circle A) and the second component (in FIG. 4, expressed with a solid circle B), the significant difference P<0.05 indicated by * was exhibited.

FIG. 5 illustrates that a change in atrial effective refractory period is shown as % change rate compared to the previous value of 100% (i.e., control value) after administering (continuous administration for 10 minutes at 0.1 mg/kg/minute, and subsequently, continuous administration for 20 minutes at 0.05 mg/kg/minute) the first optical isomer component of the present invention (in FIG. 5, expressed with an empty circle A) and the second component as the other enantiomer thereof (in FIG. 5, expressed with a solid circle B), respectively. As the result of the statistic analysis between the first optical isomer component (in FIG. 5, expressed with an empty circle A) and the second component (in FIG. 5, expressed with a solid circle B), the significant difference P<0.05 indicated by *, and the significant difference P<0.01 indicated by ** were exhibited.

FIG. 6 illustrates that a change in ventricular effective refractory period of the first optical isomer component (in FIG. 6, expressed as A on left side) and the ventricular effective refractory period of the second component as the other enantiomer thereof (in FIG. 6, expressed as B on right side) is shown as % change rate compared to the previous value of 100% (i.e., control value). An asterisk (*) indicates that there is a significant difference P<0.05 between the first component (in FIG. 6, expressed as A) and the second component (in FIG. 6, expressed as B).

FIG. 7 illustrates an elution pattern when the compound [I] is applied to chromatography using a chiral column. The first optical isomer component of the present invention is eluted at 8.1 minutes approximately, and the second optical isomer component as the other enantiomer thereof is eluted at 11.4 minutes approximately, showing that they are completely separated from each other.

FIG. 8 illustrates an elution pattern when the collected first optical isomer component of the present invention is applied to chromatography which uses the same chiral column as the one used for resolution.

FIG. 9 illustrates an elution pattern when the second optical isomer component as the other enantiomer of the first optical isomer component of the present invention is applied to chromatography which uses the same chiral column as the one used for resolution.

DESCRIPTION OF EMBODIMENTS

The optical isomers of the present invention represented by the general formula [II] include a compound which has a hydrogen atom as R in the general formula [II] and a compound which has a hydroxyl group as R in the general formula [II]. Preferred examples of the compound include a first optical isomer component of 4-[3-(4-benzylpiperidin-1-yl)propionyl]-7-methoxy-2,3,4,5-tetrahydro-1,4-benzo-thiazepine-1-oxide that is represented by the following formula [IV] or a pharmaceutically acceptable salt thereof.

[Chem. 4]

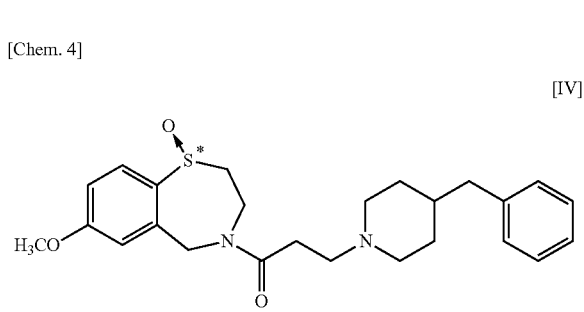 [SMILES: COc1ccc2c(c1)CN(C(=O)CCN1CCC(Cc3ccccc3)CC1)CCS2=O]

[IV]

(in the formula, * indicates a chiral center).

In the compound of the present invention, the bond (SO) between the sulfur atom (S) in the heterocyclic group and the oxygen atom (O) forms a polar atomic group showing strong electronegativity. Further, as it is a coordination bond, to show that the bond between the sulfur atom and oxygen atom is a coordination bond, it can be described as the arrow of heterocyclic S→O. Furthermore, this coordination bond can be expressed as heterocyclic S+—O−.

In general, if group $R^1$ and $R^2$ are different from each other in a sulfoxide compound represented by $R^1$—S(O)—$R^2$, it is known that the central chirality is present by having the sulfur atom as a chiral center. Namely, it is known that there are 2 types of stereoisomers, i.e., a compound in which the oxygen atom is bonded from the bottom side of a horizontal plane and a compound in which the oxygen atom is bonded from the top side of a horizontal plane. Furthermore, by ignoring the involvement of d orbital and assuming that an imaginary atom with atomic number of 0 is bonded at the position of the electron pair of the sulfur atom, it is possible to denote either R configuration or S configuration depending on the rule of order set by R—S nomenclature.

At the moment of the present invention, it is not analyzed whether the stereoisomer named as the first component of the present invention has R configuration or S configuration. However, as shown in FIG. 7, the compounds represented by the general formula [I] are found to have include two compounds that are stably and clearly separated at a temperature of 40° C. at a ratio of about 1:1 by a chiral column. Furthermore, as the collected two compounds exhibit the same behaviors according to instrumental analysis, the compounds are believed to be two types of stereoisomers based on central chirality resulting from chiral center.

In the present specification, the component eluted at 7 minutes to 9 minutes (retention time of about 8.1 minutes) when the compounds represented by the general formula [I] are loaded onto a chiral column (CHIRALPAK AD-H (manufactured by Daicel) 0.46 cm I.D.×25 cm L.) which uses MeOH/MeCN/DEA=90/10/0.1 (v/v) as a mobile phase with flow rate of 1.0 mL/min to elute the compounds at 40° C. is referred to as the first component (alternatively, also simply referred to as (A)). Further, the component subsequently eluted at 10 minutes to 13 minutes (retention time of about 11.4 minutes) is referred to as the second component (alternatively, also simply referred to as (B)). As described above, at the moment of the present invention, it is not analyzed whether the stereo configuration of the enantiomer named as the first component of the present invention has R configuration or S configuration. However, it can be collected as shown in FIG. 7 and FIG. 8, and it has been obviously isolated.

Meanwhile, an oxalate of the compound [Ia] described below forms crystal, and considering that stereoisomers at the amide portion are confirmed to be present at a ratio of about 2:3 according to $^1$H-NMR spectra recorded at room temperature, the possibility of having a nitrogen atom as the chiral center of the stereoisomers represented by the general formula [II] of the present invention cannot be completely ruled out. However, the free form of the compound [Ia] described below does not form crystal but are amorphous, and the presence of stereoisomers of which chiral center is a nitrogen atom are not confirmed.

Taken together, it is believed at the present moment that the chiral center is a sulfur atom as described above.

Since the compound of the present invention has a basic nitrogen atom, it can form an acid addition salt in this position. As an acid for forming this acid addition salt form, if it is pharmaceutically acceptable, it is not particularly limited. As a preferable acid addition salt of the present invention, examples include an inorganic acid addition salt such as hydrochloric acid salt, hydrogen bromide acid salt, sulfuric acid salt, phosphoric acid salt, or nitric acid salt; an organic acid addition salt such as oxalic acid salt, acetic acid salt, propionic acid salt, succinic acid salt, glycolic acid salt, lactic acid salt, malic acid salt, tartaric acid salt, citric acid salt, maleic acid salt, fumaric acid salt, methanesulfonic acid salt, benzene sulfonic acid salt, p-toluene sulfonic acid salt, or ascorbic acid salt; and an amino acid addition salt such as an aspartic acid salt or glutamic acid salt. Furthermore, the compound of the present invention or its acid addition salt may be a solvate like a hydrate.

The compound as the first component of the optical isomers of the present invention can be produced by separating the compounds represented by the general formula [II] by a separation method using a chiral column or the like and collecting the separated compound.

The compounds represented by the general formula [I] of the present invention can be produced by the method described in Patent Document 11. More specifically, for example, by oxidizing the compound represented by the formula [V] of the following reaction formula with a suitable oxidizing agent, an oxide represented by the formula [Ia] can be produced. As an oxidizing agent, a peroxy acid, for example, peracetic acid, perbenzoic acid, and meta-chloroperbenzoic acid (mCPBA) can be used. As a solvent, halogenated hydrocarbon such as methylene chloride or chloroform can be used as appropriate. In order to prevent oxidation to a sulfone, the reaction temperature is preferably low temperature, for example, 0° C. to 5° C. or so. From a reaction mixture, separation and purification of a target product can be carried out by publicly known separation and purification means such as extract operation, chromatography, or distillation.

[Chem. 5]

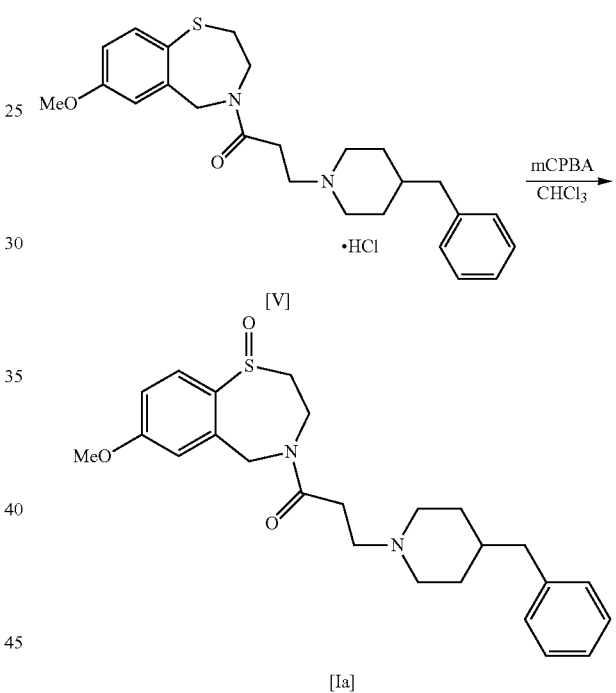

Production can be made by oxidizing the sulfur atom of the heterocycle of 4-[3-(4-benzylpiperidin-1-yl)propionyl]-7-methoxy-2,3,4,5-tetrahydro-1,4-benzothiazepine of the compound [V] by meta-chloroperbenzoic acid (mCPBA) as an oxidizing agent in chloroform (CHCl$_3$) solvent.

According to the above-mentioned reaction pathway, the hydrochloric acid salt shown by formula [V] is oxidized in chloroform solvent with meta-chloroperbenzoic acid (mCPBA) as an oxidizing agent to provide 4-[3-(4-benzylpiperidin-1-yl)propionyl]-7-methoxy-2,3,4,5-tetrahydro-1,4-benzothiazepine-1-oxide of the compound [Ia], which is then separated by silica gel chromatography using a chloroform-methanol mixture as a mobile phase. From the separated chloroform-methanol azeotropic solvent, the solvent is extracted by distillation and the residual solvent is removed in argon to give a final product. The compound represented by the above formula [Ia], which has been obtained as described above, has purity of 90% or more and has a molecular weight of 440.61, and it is an amorphous solid, stable to oxygen, humidity, acid, and alkali at a room temperature, is easily dissolved in ethanol and dimethyl sulfoxide (DMSO), and has a skin irritating property. Furthermore, the oxalate of the compound [Ia] is a crystal which has a molecular weight of 530.65, has purity of 90% or more and the melting point of 167 to 168° C., and it is soluble in water, ethanol, and dimethyl sulfoxide. It was confirmed by the analysis of the $^1$H-NMR spectra at the room temperature that the stereoisomers in an amide portion exists at ratio of about 2:3.

Furthermore, 4-{3-[4-(4-hydroxybenzyl)piperidin-1-yl] propionyl}-7-methoxy-2,3,4,5-tetrahydro-1,4-benzothiazepine-1-oxide which is a compound represented by the general formula [II] of the present invention having hydroxyl group as R, or a pharmaceutically acceptable salt thereof can be produced by the same oxidation reaction as described above while protecting the hydroxyl group, if necessary. Furthermore, a rat or a dog is administered with the 1,4-benzothiazepine derivative, which is the parent compound, and after adding water to the obtained urine or feces followed by homogenization, the supernatant can be subjected to component separation with retention time of 19 to 22 minutes by high performance liquid chromatography using a gradient elution, which uses reverse phase column using silica gel modified with octadecyl group (ODS) and, as a mobile phase, water containing 0.1% trifluoroacetic acid (TFA) as solution A and acetonitrile containing 0.1% TFA as solution B. The separated component has mass charge ratio (m/Z) of 457 according to mass spectrometry. Meanwhile, the compound of [Ia] can be also obtained by, according to the same method as above, the component separation with retention time of 27 to 30 minutes by high performance liquid chromatography using a gradient elution.

Furthermore, it is also possible to consider a method of producing a compound of the general formula [II] of the present invention by oxidizing 7-methoxy-2,3,4,5-tetrahydro-1,4-benzothiazepine by the same method as above to obtain 7-methoxy-2,3,4,5-tetrahydro-1,4-benzothiazepine-1-oxide, separating a stereoisomer therefrom by a chiral column, collecting one enantiomer, and carrying out amidation of the enantiomer at suitable reaction conditions.

The first optical isomer component of the compound represented by the general formula [II] of the preset invention or a salt thereof is useful as a therapeutic agent or a prophylactic agent for a heart disorder such as arrhythmia, heart failure, angina pectoris, or myocardial infarction, in particular, as a therapeutic agent or a prophylactic agent for a heart disorder such as arrhythmia, heart failure, angina pectoris, or myocardial infarction caused by atrial fibrillation or atrial flutter.

Thus, the first optical isomer component of the compound represented by the general formula [II] of the preset invention or a salt thereof can be used as an effective ingredient of a pharmaceutical composition. The pharmaceutical composition of the present invention can be administered orally, sublingually, or intravenously, or as a plaster, however, it is preferably administered by intracoronary artery injection.

When the pharmaceutical composition of the present invention is prepared as a solid dosage form for oral administration, it is possible to have a dosage form such as tablet, pill, powder, or granule form. In such a solid composition, one or more of the active ingredient is admixed with at least one inactive diluent agent, dispersing agent, adsorbent, for example, lactose, mannitol, glucose, hydroxypropyl cellulose, microcrystalline cellulose, starch, polyvinylpyrrolidone, magnesium aluminometasilicate, or silicic anhydride powder, or the like, and the solid composition can be produced in accordance with a conventional method.

When solid dosage forms are prepared as a tablet or a pill, coating may be carried out with a membrane of stomach-soluble or intestine-soluble film consisting of white sugar, gelatin, hydroxypropyl-cellulose, or hydroxymethylcellulose phthalate, or the like, and the coating may be carried out to have two or more layers. It is also possible to be made from a capsule such as gelatin or ethylcellulose.

When liquid dosage forms for oral administration are prepared, it is possible to have dosage forms such as pharmaceutically acceptable emulsions, solutions, suspensions, syrups, or elixir agents. As a diluent agent to be used, there is purified water, ethanol, vegetable oil, or an emulsifier, for example. Furthermore, the composition may be admixed with adjuvants such as permeation agents, suspending agents, sweetening agents, flavoring agents, aromatic agents, or antiseptic agents, in addition to the diluent agents.

When injection solutions for parenteral administration are prepared, sterile and aqueous or non-aqueous solution agents, solubilizing agents, suspensions, or emulsifiers are used. In case of aqueous solution agents, solubilizing agents, and suspensions, there are, for example, water for injection, distilled water for injection, physiological saline, cyclodextrin and its derivative, and organic amines such as triethanolamine, diethanolamine, monoethanolamine, or triethylamine, or inorganic alkali solutions.

When water-soluble solutions are prepared, for example, propylene glycol, polyethylene glycol, vegetable oil like olive oil, or alcohols like ethanol may be used. Furthermore, as a solubilizing agent, for example, surface active agents (for forming mixed micelle) such as polyoxyethylene hydrogenated castor oil or sucrose fatty acid ester, or lecithin or hydrogenated lecithin (for forming liposome) may be used. Furthermore, it is also possible to prepare emulsion agents which consists of non-water soluble solubilizing agents like vegetable oil, and lecithin, polyoxyethylene hydrogenated castor oil, polyoxyethylene polyoxypropylene glycol or the like.

The compound represented by the general formula [II] of the present invention or a salt thereof may be generally administered once daily or divided into several times per day and either orally or parenterally, within a range of 0.1 mg to 1 g, preferably 1 mg to 1 g or 0.1 mg to 0.5 g as a free compound per an adult patient per day, although it may vary depending on age, body weight, symptom, therapeutic effect, administration method, a treatment time, or the like.

Hereinafter, the present invention is further specifically explained in view of one example of the present invention. However, it is evident that the present invention is not limited at all by the following exemplifications and explanations.

Example 1

Production of the 4-[3-(4-benzylpiperidin-1-yl)propionyl]-7-methoxy-2,3,4,5-tetrahydro-1,4-benzothiazepine-1-oxide of the compound represented by formula [Ia]

30.0 g of hydrochloride salt of 4-[3-(4-benzylpiperidin-1-yl)propionyl]-7-methoxy-2,3,4,5-tetrahydro-1,4-benzothiazepine, which is the compound shown by the above formula [V], was added to a reaction vessel, to which 800 ml of chloroform ($CHCl_3$) as a solvent was added, and dissolved under stirring at room temperature. Subsequently, the reaction vessel was placed in an ice-cold water bath, and it was cooled until the temperature inside the vessel becomes 0 to 1° C. Six hundred ml of chloroform ($CHCl_3$) solution dissolved with 14.0 g of meta-chloroperbenzoic acid (mCPBA) was gradually added dropwise thereto with dropwise addition time of 110 minutes while being careful not to have an increase of the reaction temperature. After completion of the dropwise addition, stirring was performed at 0 to 1° C. for 20 minutes approximately.

Subsequently, 200 ml of $H_2O$ solution dissolved with 4.14 g of $Na_2SO_3$ was added dropwise thereto at 0 to 5° C. over 1 minute. After completion of the dropwise addition, stirring was performed at 0 to 5° C. for 10 minutes. Subsequently, while maintaining it cool at 0 to 5° C., 1 mol/liter aqueous solution of NaOH was added dropwise thereto over 1 minute. After the dropwise addition, stirring was performed at 0 to 5° C. for 15 to 20 minutes. After separating out the organic layer, the aqueous layer was extracted with 600 ml of $CHCl_3$. The organic layer was combined with extracts and washed once with 200 ml of $H_2O$ and once with 200 ml of saturated NaCl solution. The organic layer was dried with anhydrous $Na_2SO_4$, and then concentrated under reduced pressure.

By the silica gel chromatography, concentrated residue was eluted by ethanol for purification. The objective compound was obtained at 13 g as an amorphous to viscous oil phase.

IR ($cm^{-1}$): 3452, 2919, 1643, 1594, 1022
$^1$H-NMR ($CDCl_3$, 300 MHz): δ
1.1-2.95 (17H, m), 3.78 (3H, s), 3.86-4.16 (2H, m), 4.65 (2H, s), 6.8-7.65 (8H, m)
MS (FD-MS): 441 (M')

Example 2

The first optical isomer component and the second component of the compounds represented by the formula [IV] of the present invention were prepared by separating the compound represented by the formula [Ia], which has been prepared in Example 1, and then by collecting, at the conditions described below.

Column: CHIRALPAK AD-H (manufactured by Daicel Corporation)
Size: 0.46 cm I.D.×25 cm L.
Mobile phase: MeOH/MeCN/DEA=90/10/0.1 (v/v)
Flow rate: 1.0 mL/min
Temperature: 40° C.
Detection wavelength: 245 nm
Injection amount: 10 μL MeOH represents methanol, MeCN represents acetonitrile, and DEA represents diethylamine, respectively.

Meanwhile, as for the devices, the followings were used.
Pump: LC-20AD (manufactured by Shimadzu Corporation)
Detector: SPD-20A (manufactured by Shimadzu Corporation)
Auto sampler: SIL-20A (manufactured by Shimadzu Corporation)

From 10 g of the compound represented by the formula [Ia], it was possible to collect the first optical isomer component and the second component, each in an amount of 4 g.

Each of the collected components was applied to column chromatography at the same conditions as above. The results are shown in FIG. 8 and FIG. 9, respectively.

Example 3

Measurement of heart rate, blood pressure, left ventricular contraction function (max dP/dt), and left ventricular relaxation function (min dP/dt)

Test method: In the present test, by using an anaesthetized rat, the influence of the hydrochloride salt of the first optical isomer component (A) and the second optical isomer component (B), each administered intravenously and continuously, on a circulatory system was determined. The test was performed with n=5 for each group. Each of the first component (A) or the second component (B) was continuously administered for 20 minutes at 0.1 mg/kg/minute, and then the measurement of heart rate, blood pressure, max dP/dt, and min dP/dt was performed. Each parameter was measured at 0 minute, 1 minute, 5 minutes, 10 minutes, 15 minutes, 20 minutes, 25 minutes, 30 minutes, 35 minutes, and 40 minutes after the administration, and the result was expressed in terms of a difference compared to the 0 minute value (previous value (i.e., control value)). The measurement value was expressed in terms of mean value±SD.

Test results: The result relating to a change in the heart rate is shown in FIG. 1. As shown in FIG. 1, the heart rate was mildly increased by the first optical isomer component (A) but the heart rate was decreased by the second optical isomer component (B), showing the pharmacological activities that are contradictory to each other.

The result relating to a change in blood pressure is shown in FIG. 2. As shown in FIG. 2, the blood pressure was mildly increased by the first optical isomer component (A) but the blood pressure was decreased by the second optical isomer component (B), showing the pharmacological activities that are contradictory to each other.

The change in left ventricular contraction function is shown in FIG. 3. As shown in FIG. 3, the left ventricular contraction function was enhanced by the first optical isomer component (A) but the left ventricular contraction function was reduced by the second optical isomer component (B), showing the pharmacological activities that are contradictory to each other.

The change in left ventricular relaxation function is shown in FIG. 4. As shown in FIG. 4, the left ventricular relaxation function was enhanced by the first optical isomer component (A) but the left ventricular relaxation function was reduced by the second optical isomer component (B), showing the pharmacological activities that are contradictory to each other.

For the data of FIG. 1 to FIG. 4, determination of a significant difference was carried out by using t test.

Example 4

Influence on Atrial Effective Refractory Period

Test method: In the present test, by using an anaesthetized beagle dog, the influence of hydrochloride salt of the first optical isomer component (A) and the second optical isomer component (B), each administered intravenously and continuously, on atrial effective refractory period was determined. The test was performed with n=5 for each group. The test compound was continuously administered for 10 minutes at 0.1 mg/kg/minute and then for 20 minutes at 0.05 mg/kg/minute. Measurement of atrial effective refractory period till 270 minutes after the termination of the administration was carried out. The pacing interval was 250 msec. The measurement value was expressed in terms of mean value±SD.

Test results: The test results are expressed in terms of % change rate when the previous value (i.e., control value) of atrial effective refractory period is set at 100%. The results are shown in FIG. 5. As shown in FIG. 5, the atrial effective refractory period was extended by the first optical isomer component (A) and also by the second optical isomer component (B), and the longer extension was obtained by the first optical isomer component (A).

For the data of FIG. 5, determination of a significant difference was carried out by using t test.

Example 5

Influence on Ventricular Effective Refractory Period

Test method: In the present test, by using an anaesthetized beagle dog, the influence of the first optical isomer component (A) and the second optical isomer component (B), each administered intravenously and rapidly, on ventricular effective refractory period was determined. The test was performed with n=5 for each group. The test compound was rapidly administered for 5 minutes at 1 mg/kg/minute. Measurement of ventricular effective refractory period was carried out immediately after the termination of the administration. The pacing interval was 250 msec. The measurement value was expressed in terms of mean value±SD.

Test results: The test results are expressed in terms of % change rate when the previous value (i.e., control value) of ventricular effective refractory period is set at 100%. The results are shown in FIG. 6. As shown in FIG. 6, the ventricular effective refractory period was not extended by the first optical isomer component (A), but it was significantly extended by the second optical isomer component (B) (P<0.05).

INDUSTRIAL APPLICABILITY

The present invention is to provide a compound having a specific stereo configuration and a property of an ideal therapeutic agent for atrial fibrillation which can extend atrial effective refractory period but does not extend ventricular effective refractory period and a pharmaceutical composition using the compound, and they are useful in the field of pharmaceuticals and medicines and thus have an industrial applicability.

The invention claimed is:
1. An optical isomer of a compound having formula [II] or a pharmaceutically acceptable salt thereof;

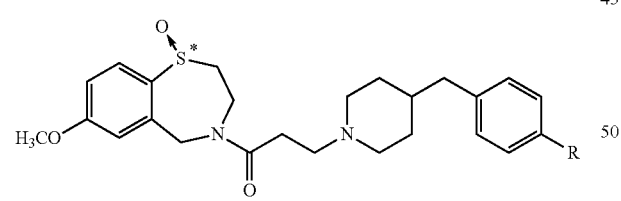

[II]

wherein in the formula, R presents a hydrogen atom or a hydroxyl group, and * indicates the presence of optical isomers, and
wherein the optical isomer of the compound is a first optical isomer component which is the first eluted enantiomer when two enantiomers are separated by using a chiral column at conditions described below,
chromatography: normal-phase chromatography,
mobile phase: organic solvents comprising methanol/acetonitrile, and
stationary phase: amylose tris-(3,5-dimethylphenylcarbamate) coated silica-gel.

2. The optical isomer of the compound or the pharmaceutically acceptable salt thereof according to claim 1, wherein the pharmaceutically acceptable salt is hydrochloride salt or citrate salt.

3. A pharmaceutical composition comprising the optical isomer of the compound or the pharmaceutically acceptable salt thereof according to claim 1, and a pharmaceutically acceptable carrier.

4. A method for producing first and second optical isomer compounds each having formula [II] comprising:

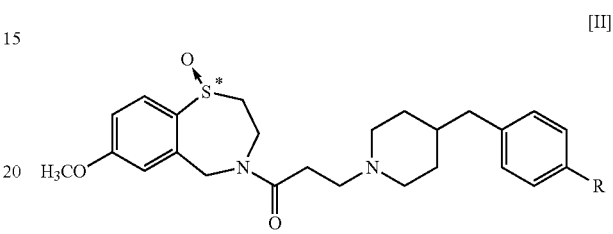

[II]

wherein in the formula, R presents a hydrogen atom or a hydroxyl group, and * indicates the presence of optical isomers,
resolving a compound having formula [I] by using a chiral column

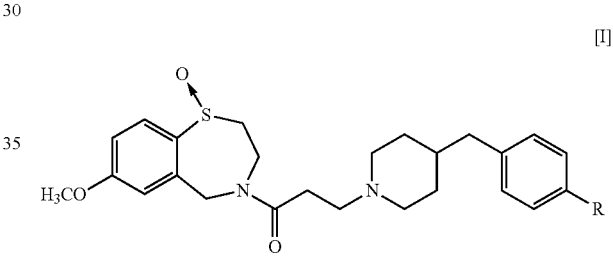

[I]

wherein in the formula, R presents a hydrogen atom or a hydroxyl group; and
collecting first and second optical isomer component fractions eluted from the chiral column, wherein the first optical isomer component is the first eluted enantiomer when two enantiomers are separated by using the chiral column at conditions described below,
chromatography: normal-phase chromatography,
mobile phase: organic solvents comprising methanol/acetonitrile, and
stationary phase: amylose tris-(3,5-dimethylphenylcarbamate) coated silica-gel.

5. The optical isomer of the compound or the pharmaceutically acceptable salt thereof according to claim 2, wherein the pharmaceutically acceptable salt is hydrochloride salt.

6. The pharmaceutical composition according to claim 3, wherein the pharmaceutically acceptable salt is hydrochloride salt or citrate salt.

7. The pharmaceutical composition according to claim 6, wherein the pharmaceutically acceptable salt is hydrochloride salt.

* * * * *